(12) United States Patent
Banet

(10) Patent No.: US 7,481,772 B2
(45) Date of Patent: Jan. 27, 2009

(54) VITAL SIGNS MONITOR USED FOR CONDITIONING A PATIENT'S RESPONSE

(75) Inventor: Matthew John Banet, Del Mar, CA (US)

(73) Assignee: Triage Wireless, Inc., San Diego, CA (US)

( * ) Notice: Subject to any disclaimer, the term of this patent is extended or adjusted under 35 U.S.C. 154(b) by 0 days.

(21) Appl. No.: 11/160,942

(22) Filed: Jul. 15, 2005

(65) Prior Publication Data

US 2005/0261594 A1    Nov. 24, 2005

Related U.S. Application Data

(63) Continuation of application No. 10/906,665, filed on Mar. 1, 2005, which is a continuation-in-part of application No. 10/752,198, filed on Jan. 6, 2004, now Pat. No. 7,396,330.

(51) Int. Cl.
*A61B 5/00* (2006.01)

(52) U.S. Cl. .................. 600/500; 600/485; 600/503

(58) Field of Classification Search .................. None
See application file for complete search history.

(56) References Cited

U.S. PATENT DOCUMENTS

| | | | |
|---|---|---|---|
| 3,412,729 A | 11/1968 | Smith | |
| 4,063,551 A | 12/1977 | Sweeney | |
| 4,080,966 A | 3/1978 | McNally et al. | |
| 4,083,366 A * | 4/1978 | Gombrich et al. | 600/503 |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,681,118 A | 7/1987 | Asia et al. | |
| 4,777,954 A | 10/1988 | Kuesch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 5,002,055 A | 3/1991 | Merki et al. | |
| 5,038,792 A | 8/1991 | Mault | |
| 5,111,817 A | 5/1992 | Clark et al. | |
| 5,140,990 A | 8/1992 | Jones et al. | |
| 5,178,155 A | 1/1993 | Mault | |

(Continued)

OTHER PUBLICATIONS

Yang, Boo-Ho et al., Cuff-Less Continious Monitoring of Beat-To-Beat Pressure Using Sensor Fusion, submitted to IEEE Transactions on Biomedical Engineering.

(Continued)

*Primary Examiner*—Robert L Nasser
(74) *Attorney, Agent, or Firm*—Wilmer Cutler Pickering Hale & Dorr LLP

(57) ABSTRACT

The invention provides a method for monitoring a patient, comprising the following steps: 1) outfitting the patient with a ambulatory blood pressure monitor that features an optical system for measuring blood pressure without using a cuff, and a wireless system configured to send and receive information sent from an Internet-based system through a wireless network; 2) sending from the Internet-based system to the ambulatory blood pressure monitor a signal that indicates a blood pressure level; 3) comparing a blood pressure value measured with the ambulatory blood pressure monitor to the blood pressure level; and 4) generating a signal in response to the comparing step.

3 Claims, 3 Drawing Sheets

U.S. PATENT DOCUMENTS

| | | | |
|---|---|---|---|
| 5,179,958 A | 1/1993 | Mault | |
| 5,213,099 A | 5/1993 | Tripp, Jr. | |
| 5,237,997 A | 8/1993 | Greubel et al. | |
| 5,309,916 A | 5/1994 | Hatschek | |
| 5,316,008 A * | 5/1994 | Suga et al. | 600/513 |
| 5,368,039 A | 11/1994 | Moses | |
| 5,435,315 A | 7/1995 | McPhee et al. | |
| 5,485,848 A | 1/1996 | Jackson et al. | |
| 5,551,438 A | 9/1996 | Moses | |
| 5,632,272 A | 5/1997 | Diab et al. | |
| 5,727,558 A | 3/1998 | Hakki et al. | |
| 5,743,857 A | 4/1998 | Shinoda et al. | |
| 5,788,634 A * | 8/1998 | Suda et al. | 600/382 |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,891,042 A | 4/1999 | Sham et al. | |
| 5,897,493 A | 4/1999 | Brown | |
| 5,921,936 A | 7/1999 | Inukai et al. | |
| 5,997,476 A | 12/1999 | Brown | |
| 6,004,274 A | 12/1999 | Nolan et al. | |
| 6,013,009 A | 1/2000 | Karkanen | |
| 6,024,699 A | 2/2000 | Surwit et al. | |
| 6,050,940 A | 4/2000 | Braun et al. | |
| 6,095,985 A | 8/2000 | Raymond et al. | |
| 6,101,478 A | 8/2000 | Brown | |
| 6,120,459 A * | 9/2000 | Nitzan et al. | 600/493 |
| 6,168,563 B1 | 1/2001 | Brown | |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,272,936 B1 | 8/2001 | Oreper | |
| 6,280,390 B1 | 8/2001 | Akselrod et al. | |
| 6,282,441 B1 | 8/2001 | Raymond et al. | |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,368,273 B1 | 4/2002 | Brown | |
| 6,371,921 B1 | 4/2002 | Caro et al. | |
| 6,375,614 B1 | 4/2002 | Braun et al. | |
| 6,398,727 B1 * | 6/2002 | Bui et al. | 600/300 |
| 6,413,223 B1 | 7/2002 | Yang et al. | |
| 6,432,061 B1 | 8/2002 | Nissila et al. | |
| 6,443,890 B1 | 9/2002 | Schulze et al. | |
| 6,443,905 B1 | 9/2002 | Nissila et al. | |
| 6,443,906 B1 | 9/2002 | Ting et al. | |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,511,436 B1 | 1/2003 | Asmar | |
| 6,514,211 B1 | 2/2003 | Baura | |
| 6,527,711 B1 | 3/2003 | Stivoric et al. | |
| 6,533,729 B1 | 3/2003 | Khair et al. | |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,579,231 B1 | 6/2003 | Phipps | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 | 9/2003 | Goodman | |
| 6,645,154 B2 | 11/2003 | Oka | |
| 6,645,155 B2 | 11/2003 | Inukai et al. | |
| 6,652,466 B2 | 11/2003 | Sugo et al. | |
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,733,447 B2 | 5/2004 | Lai et al. | |
| 6,740,045 B2 | 5/2004 | Amano | |
| 6,775,566 B2 | 8/2004 | Nissila et al. | |
| 6,790,178 B1 | 9/2004 | Mault et al. | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 | 2/2005 | Caro et al. | |
| 6,871,084 B1 | 3/2005 | Kigsley et al. | |
| 2002/0183627 A1 * | 12/2002 | Nishii et al. | 600/485 |
| 2004/0030261 A1 | 2/2004 | Rantala | |
| 2004/0260186 A1 | 12/2004 | Dekker | |
| 2005/0131308 A1 | 6/2005 | Chio et al. | |

OTHER PUBLICATIONS

Weijia Cui, Lee E. et al., In Vivo Reflectance of Blood and Tissue as a Function of Light Wavelength, submitted to IEEE Transactions of Biomedical Engineering, vol. 37 No. 6.

* cited by examiner

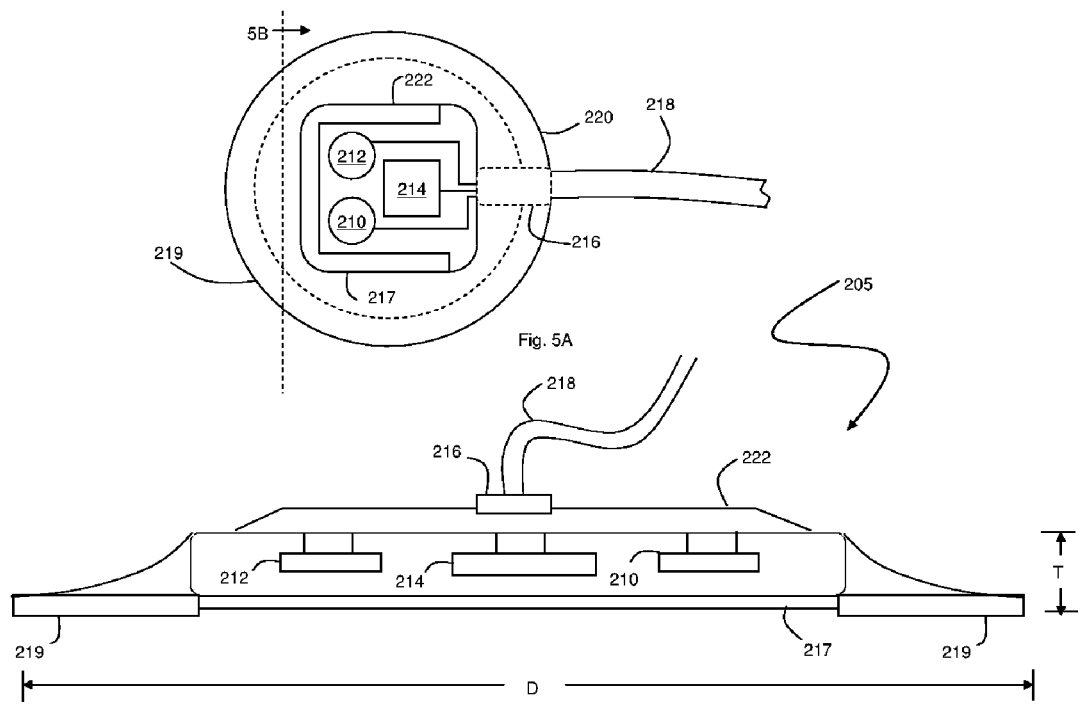
Fig. 5A
Fig. 5B
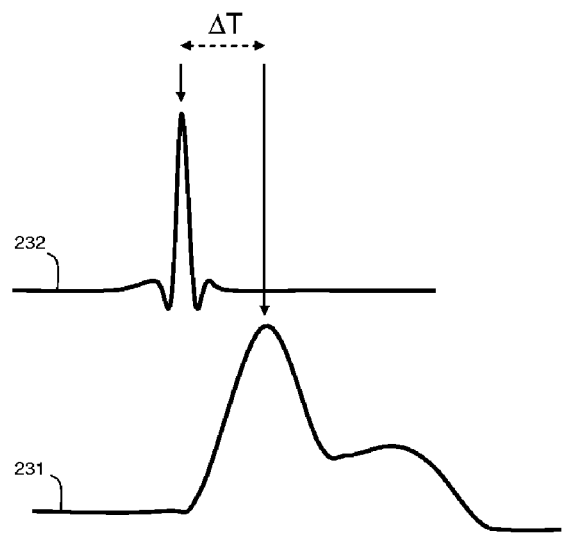
Fig. 6

VITAL SIGNS MONITOR USED FOR CONDITIONING A PATIENT'S RESPONSE

CROSS REFERENCES TO RELATED APPLICATION

This application is a continuation of U.S. patent application Ser. No. 10/906,665, filed Mar. 1, 2005, which is a continuation-in-part application of U.S. patent application Ser. No. 10/752,198, filed on Jan. 6, 2004 now U.S. Pat. No. 7,396,330.

BACKGROUND OF THE INVENTION

The present invention relates to medical devices for monitoring vital signs such as heart rate, pulse oximetry, and blood pressure, and using this information to condition a patient's response.

DESCRIPTION OF THE RELATED ART

Pulse oximeters are medical devices featuring an optical module, typically worn on a patient's finger or ear lobe, and a processing module that analyzes data generated by the optical module. The optical module typically includes first and second light sources (e.g., light-emitting diodes, or LEDs) that transmit optical radiation at, respectively, red ($\lambda \sim 630\text{-}670$ nm) and infrared ($\lambda \sim 800\text{-}1200$ nm) wavelengths. The optical module also features a photodetector that detects radiation transmitted or reflected by an underlying artery. Typically the red and infrared LEDs sequentially emit radiation that is partially absorbed by blood flowing in the artery. The photodetector is synchronized with the LEDs to detect transmitted or reflected radiation. In response, the photodetector generates a separate radiation-induced signal for each wavelength. The signal, called a plethysmograph, varies in a time-dependent manner as each heartbeat varies the volume of arterial blood and hence the amount of transmitted or reflected radiation. A microprocessor in the pulse oximeter processes the relative absorption of red and infrared radiation to determine the oxygen saturation in the patient's blood. A number between 94%-100% is considered normal, while a value below 85% typically indicates the patient requires hospitalization. In addition, the microprocessor analyzes time-dependent features in the plethysmograph to determine the patient's heart rate.

Pulse oximeters work best when the appendage they attach to (e.g., a finger) is at rest. If the finger is moving, for example, the light source and photodetector within the optical module typically move relative to the hand. This generates 'noise' in the plethysmograph, which in turn can lead to motion-related artifacts in data describing pulse oximetry and heart rate. Ultimately this reduces the accuracy of the measurement. Various methods have been disclosed for using pulse oximeters to obtain arterial blood pressure values for a patient. One such method is disclosed in U.S. Pat. No. 5,140,990 to Jones et al., for a 'Method Of Measuring Blood Pressure With a Photoplethysmograph'. The '990 Patent discloses using a pulse oximeter with a calibrated auxiliary blood pressure monitor to generate a constant that is specific to a patient's blood pressure. Another method for using a pulse oximeter to measure blood pressure is disclosed in U.S. Pat. No. 6,616,613 to Goodman for a 'Physiological Signal Monitoring System'. The '613 Patent discloses processing a pulse oximetry signal in combination with information from a calibrating device to determine a patient's blood pressure.

BRIEF SUMMARY OF THE INVENTION

The present invention provides a cuffless blood-pressure monitor that features a behavior modification system. The blood pressure monitor is typically worn on a patient's head and makes a transdermal, optical measurement of blood pressure, which it then sends to a processing component (e.g., a PDA). The processing component preferably features an embedded, short-range wireless transceiver and a software platform that displays, analyzes, and then transmits the information through a wireless network to an Internet-based system. This system generates an audio or visual alarm when the patient's blood pressure trends high, and thus the patient may modify their behavior through conditioned response. In addition, a medical professional can continuously monitor a patient's blood pressure during their day-to-day activities. Monitoring patients in this manner minimizes erroneous measurements due to 'white coat syndrome', increases the accuracy of a blood-pressure measurement and additionally allows patients to modify behavior to lower blood pressure while wearing the device.

The invention has many advantages. In particular, one aspect of the invention provides a system that continuously monitors a patient's blood pressure using a cuffless blood pressure monitor and an off-the-shelf mobile communication device. Information describing the blood pressure can be viewed using an Internet-based website, using a personal computer, or simply by viewing a display on the mobile device. Blood-pressure information measured continuously throughout the day provides a relatively comprehensive data set compared to that measured during isolated medical appointments. This approach identifies trends in a patient's blood pressure, such as a gradual increase or decrease, which allows for the patient to view and conditionally respond to high blood pressure through behavior modification such as breathing exercises. The monitor can also characterize the patient's heart rate and blood oxygen saturation using the same optical system for the blood-pressure measurement. This information can be wirelessly transmitted along with blood-pressure information and used to further diagnose the patient's cardiac condition. The monitor is small, easily worn by the patient during periods of exercise or day-to-day activities, and makes a non-invasive blood-pressure measurement in a matter of seconds. The resulting information has many uses for patients, medical professionals, hospitals, insurance companies, pharmaceutical agencies conducting clinical trials, and organizations for home-health monitoring.

In one aspect, the invention provides a system for measuring blood pressure from a patient that features: 1) an optical module configured to be worn on (or in) the patient's head that includes at least one optical source and a photodetector; 2) a calibration source configured to make a blood pressure measurement; and, 3) a processing module configured to: i) receive a first signal from the optical module; ii) receive a second signal from the calibration source; iii) process the first and second signals to generate a calibration table; and iv) receive a third signal from the optical module and compare it to the calibration table to determine the patient's blood pressure.

The preferred invention includes a response alert system designed to alert the patient when escalated vital signs reach dangerously harmful levels. The alert system alerts the patient when blood pressure levels reach dangerous levels caused by stress and anxiety. Each patient's blood pressure level parameters are set during the time of calibration by a physician.

In embodiments, the blood pressure monitor features a head-worn clip that includes the optical module (e.g., a photodetector and first and second LEDs that emit, respectively, red radiation and infrared radiation). The optical calibration source is typically a cuff-based blood pressure module that includes a cuff and a pump worn around the patient's arm. In other embodiments, the optical module includes a short-range wireless transmitter configured to send signals to the processing module, which in turn may include a matched short-range wireless receiver.

The short-range wireless transceiver preferably operates on a wireless protocol such as Bluetooth™, 802.15.4 or 802.11. The long-range wireless transmitter preferably transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. In addition, the cuffless blood pressure-measuring device of the invention combines all the benefits of conventional cuff-based blood-pressure measuring devices without any of the obvious drawbacks (e.g., restrictive, uncomfortable cuffs). Its measurement is basically unobtrusive to the patient, and thus alleviates conditions, such as a poorly fitting cuff, that can erroneously affect a blood-pressure measurement.

The device is small and makes a non-invasive blood-pressure measurement in a matter of seconds. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure. These and other advantages of the invention will be apparent from the following detailed description and from the claims.

BRIEF DESCRIPTION OF SEVERAL VIEWS OF THE DRAWINGS

FIG. 5A is a schematic top view of an adhesive patch sensor that measures blood pressure according to the invention;

FIG. 5B is a schematic, cross-sectional view of the patch sensor of FIG. 1A; and FIG. 6 is a graph of time-dependent optical and electrical waveforms generated by the patch sensor of FIG. 5A.

DETAILED DESCRIPTION OF THE INVENTION

Figure 1:
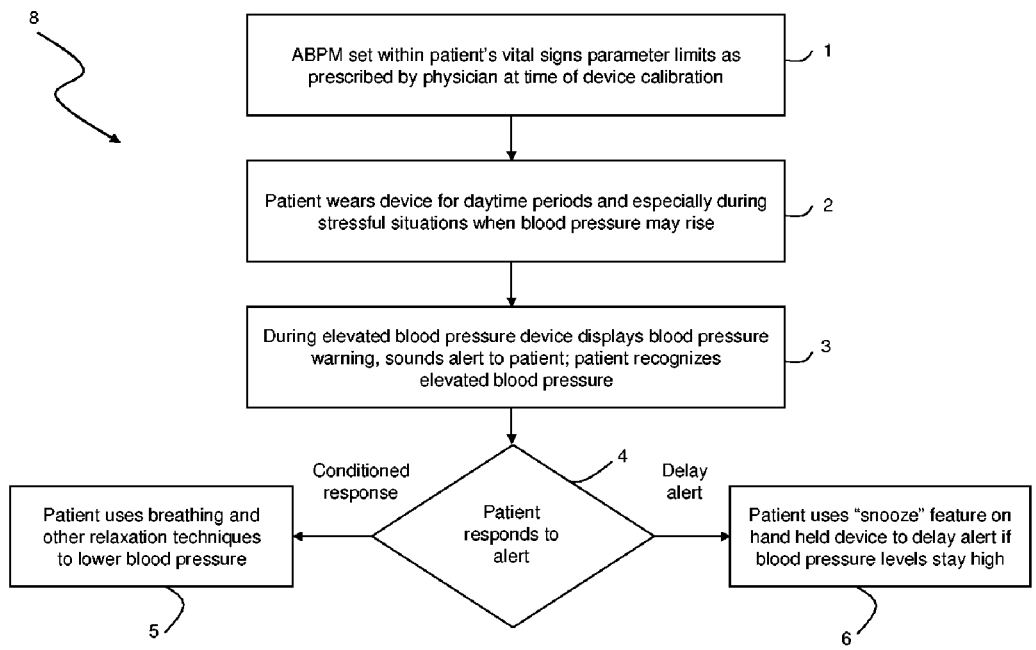
FIG. 1 is a semi-schematic diagram of a method for developing a conditioned response that utilizes the cuffless ambulatory blood-pressure monitor of the invention.

FIG. 1 shows a semi-schematic diagram illustrating a conditioned response alert system 8 that features an ambulatory blood pressure monitor (ABPM) according to the invention. In preferred embodiments, a physician prescribes to a patient an ABPM that identifies harmfully high blood pressure levels using the conditioned response alert system 8. While outfitting the patient, the physician sets vital signs parameter limits, e.g. blood pressure limits, into the ABPM that indicate when an audio alarm will sound (step 1). Patients typically wear the ABPM for an extended period of time, during which they are typically exposed to stressful situations that may cause their blood pressure to rise (step 2). As blood pressure levels elevate into dangerously high levels, the ABPM emits an audio response and/or a visual alert that indicates high blood pressure levels (step 3). The patient responds to the alert (step 4) by, e.g., using breathing and other relaxation techniques to lower their blood pressure (step 5), or by activating a 'snooze' feature on the monitor to delay the alert (step 6). Over time the patient develops a conditioned response to the alert and becomes aware that their blood-pressure levels are dangerously high. Ultimately this lowers the patient's blood pressure, thereby reducing the chance that a serious medical condition, e.g. heart attack or stroke, occurs.

Figures 2A, 2B:
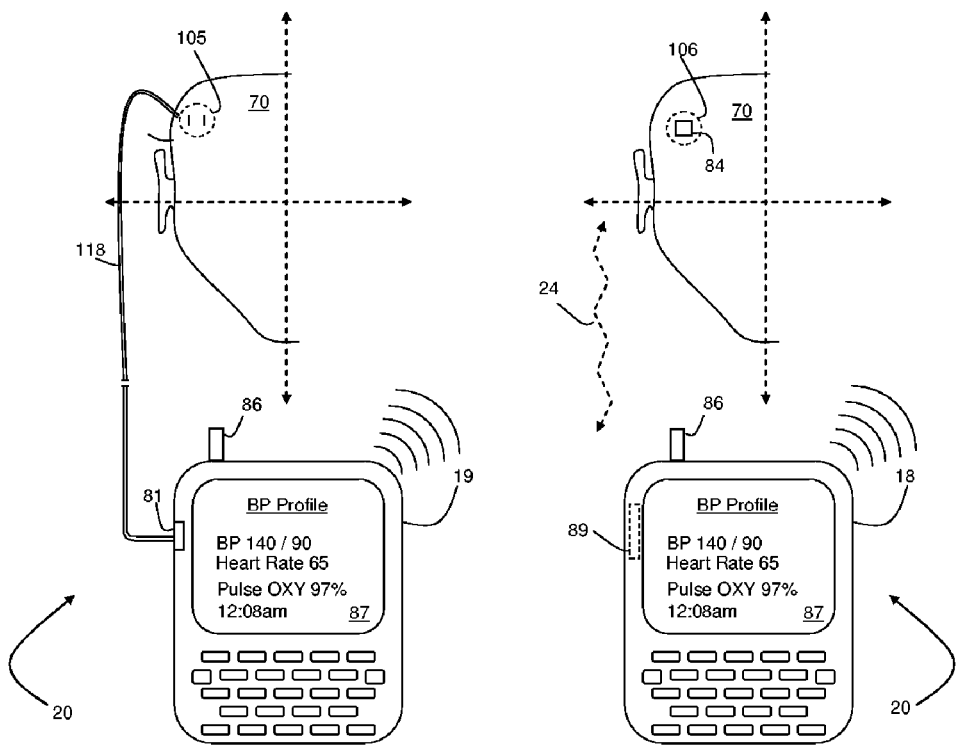
FIGS. 2A and 2B are semi-schematic views of the cuffless ambulatory blood-pressure monitor of FIG. 1 featuring a head-band with an optical system and a wireless hub connected, respectively, by a cable and short-range wireless connection.

As shown in FIGS. 2A and 2B, the ABPM 20 typically features an optical head-mounted component 105 that attaches to a patient's head 70, and a processing component 19 that preferably attaches to the patient's belt. In a preferred embodiment, a cable 118 provides an electrical connection 81 between the head-mounted component 105 and the processing component 19. During operation, the head-mounted component 105 measures optical and electrical 'waveforms', described in more detail below, that the processing component 19 processes to determine real-time beat-to-beat diastolic and systolic blood pressure, heart rate, and pulse oximetry. The processing component also includes an internal wireless system that relays this information to an Internet-based system through an antenna 86.

Methods for processing the optical and electrical waveform to determine blood pressure are described in the following co-pending patent applications, the entire contents of which are incorporated by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL-SIGN MONITOR FOR ATHLETIC APPLICATIONS (U.S. Ser. No.; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); and 8) PATCH SENSOR FOR MEASURING BLOOD PRESSURE WITHOUT A CUFF (U.S. Ser. No. 10/906,315; filed Feb. 14, 2005).

FIG. 2B shows an alternate embodiment of the invention wherein an optical patch sensor 106 sends vital-sign information to a processing component 18 using a short-range wireless link 24. In this embodiment the optical patch sensor 106 includes a short-range wireless transmitter 84, and the processing component 18 features an embedded, matched short-range wireless transceiver 89. The optical patch sensor 106 attaches free from wires to the patient's forehead 70 to increase mobility and flexibility. The short-range wireless transceiver 89 is preferably a transmitter operating on a wireless protocol, e.g. Bluetooth™, 802.15.4 or 802.11. A preferred processing component 18 is a personal digital assistant (PDA) or cellular phone that operates with the above-described ABPM with little or no modifications. For example, the processing component 18 can be a PDA that includes a wireless CDMA chipset, such as the MSM family of mobile processors manufactured by Qualcomm, each of which includes an internal Bluetooth™ radio. Suitable chipset within this family include the MSM6025, MSM6050, and the MSM6500, and are described and compared in detail in http://www.gualcomm.com. In addition to circuit-switched voice calls, the wireless transmitters used in these chipsets transmit data in the form of packets at speeds up to 307 kbps in mobile environments.

The processing component 18 preferably supports a custom firmware application that displays and analyzes information for the ABPM 20. The firmware application is typically written to operate on a variety of mobile device operating systems including BREW, Palm OS, Java, Pocket PC, Windows CE, and Symbian. A more detailed explanation of the custom firmware application is disclosed in co-pending U.S. patent application Ser. No. 10/967,511, filed on Oct. 18, 2004, for a CUFFLESS BLOOD-PRESSURE MONITOR AND ACCOMPANYING WIRELESS MOBILE DEVICE, the contents of which have been previously incorporated by reference.

Figure 3:
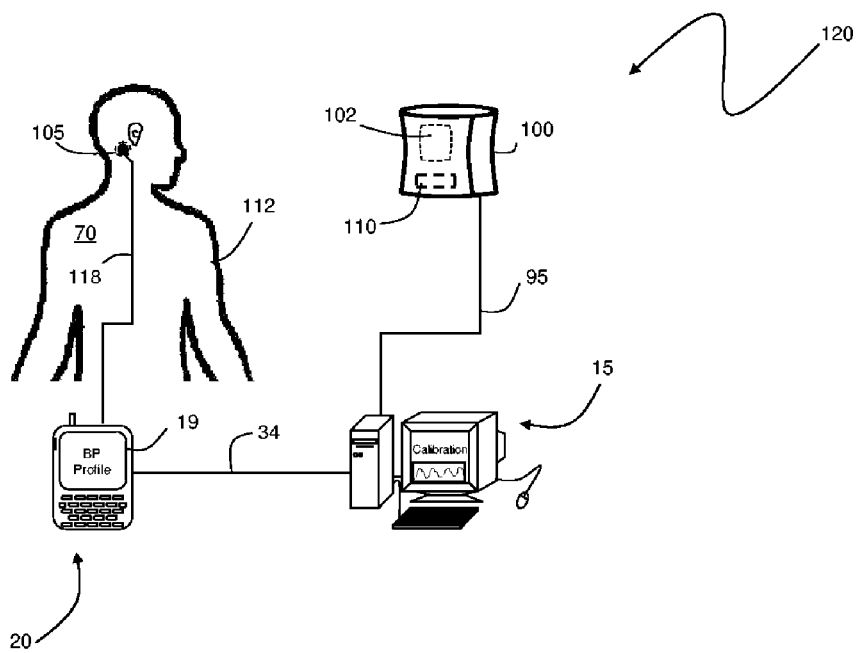
FIG. 3 is a semi-schematic view of a calibration process used with the ambulatory blood-pressure monitor of FIGS. 2A and 2B.

FIG. 3 shows a system 120 wherein a physician calibrates the above-described ABPM 20 for a particular patient 70 and additionally enters blood pressure limits used in the conditioned response alert system. In a preferred embodiment, the physician initiates the calibration process using a personal computer 1 5 that sends a signal through a wired connection 34 to a processing component 19 within the ABPM 20. In response, the processing component 19 measures and processes optical and electrical waveforms collected by the optical patch sensor 105 to determine the patient's calibration parameters. These calibration parameters are described in more detail in BLOOD PRESSURE MONITORING DEVICE FEATURING A CALIBRATION-BASED ANALYSIS (U.S. Ser. No. 10/967,610; filed Oct. 18, 2004) and PATCH SENSOR FOR MEASURING BLOOD PRESSURE WITHOUT A CUFF (U.S. Ser. No. 10/906,315; filed Feb. 14, 2005), the contents of which have been previously incorporated herein by reference. The system 120 correlates the calibration parameters to blood pressure by subsequently measuring the patient's blood pressure using a calibration device 100, typically a conventional blood-pressure cuff, which temporarily attaches to an upper portion 112 of the patient's arm. Immediately after measuring the calibration parameters, the personal computer 15 sends a second signal through a second wired connection 95 to a controller 110 embedded within the calibration device 100. The signal directs the controller 110 to initiate the cuff-based blood pressure measurement using a motor-controlled pump 102. Once the signal is received, the calibration device 100 collects blood pressure values (e.g. systolic and diastolic pressures), and sends these back through the wired connection 95 to the personal computer 15. The system 120 repeats this process at a later time (e.g., 15 minutes later) to collect a second set of calibration parameters. The physician then removes the calibration device 100. The personal computer 15 then calculates a calibration table associating the calibration parameters and blood pressure values that passes through the wired connection 34 to the processing component 19 within the ABPM, where it is stored in memory. The ABPM uses the calibration table for all future cuffless measurements of blood pressure.

Once the ABPM 20 is calibrated, the physician enters blood pressure limits into the personal computer 15. The blood pressure limits pass through the wired connection 34 to the processing component 19, where they are stored in memory. During an actual measurement, the processing module 19 compares the patient's blood pressure measured with the ABPM 20 to the blood pressure limits stored in memory to determine if the patient's blood pressure is trending high or low. If this is the case, the controller 19 initiates an audio and/or visual alert as described above.

Figure 4:
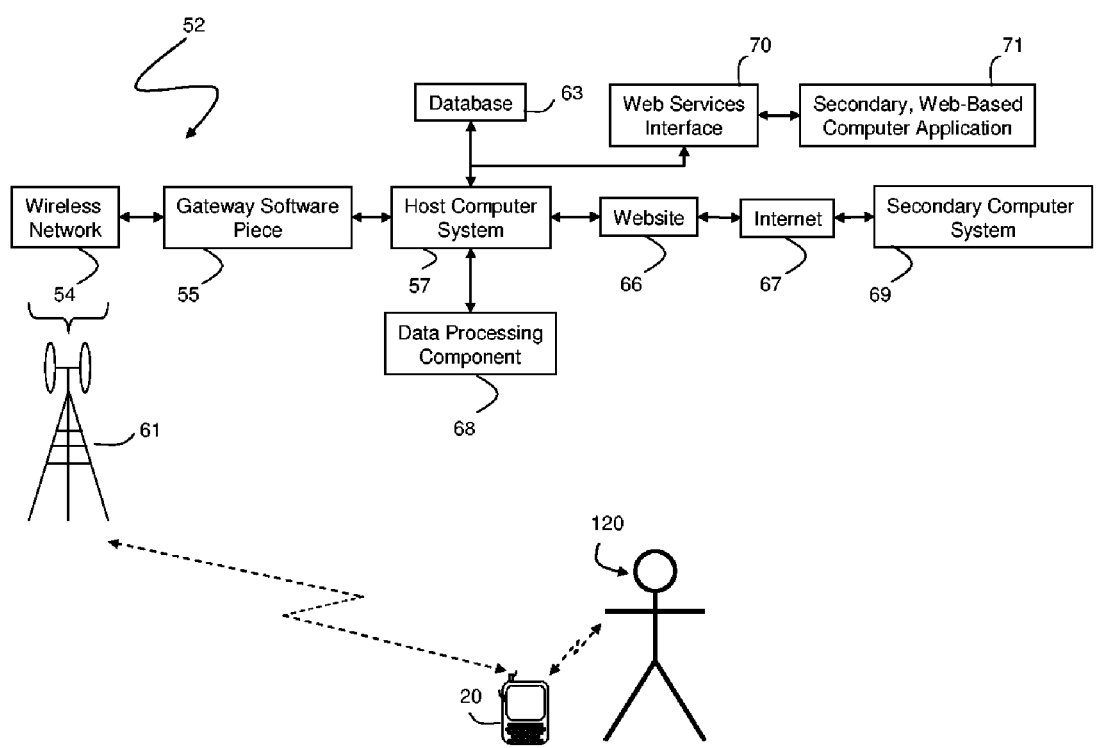
FIG. 4 is a schematic view of an Internet-based system that operates with the ambulatory blood-pressure monitor of FIGS. 2A and 2B.

FIG. 4 shows a preferred embodiment of an Internet-based system 53 that operates in concert with the ABPM 20 to send information from a patient through a wireless network 54 to a web site 66 hosted on an Internet-based host computer system 57. A secondary computer system 69 accesses the website 66 through the Internet 67. The system 53 functions in a bi-directional manner, i.e. the ABPM 20 can both send and receive data. Most data flows from the ABPM 20; using the same network, however, the monitor 20 can also receive data (e.g., calibration parameters, pre-determined blood pressure levels, software upgrades, and text messages indicating 'alerts' or trending blood pressure) through the wireless network 54. A wireless gateway 55 connects to the wireless network 54 and receives data from one or more ABPMs. The wireless gateway 55 additionally connects to a host computer system 57 that includes a database 63 and a data-processing component 68 for, respectively, storing and analyzing the data. The host computer system 57, for example, may include multiple computers, software pieces, and other signal-processing and switching equipment, such as routers and digital signal processors. The wireless gateway 55 preferably connects to the wireless network 54 using a TCP/IP-based connection, or with a dedicated, digital leased line (e.g., a frame-relay circuit or a digital line running an X.25 or other protocols). The host computer system 57 also hosts the web site 66 using conventional computer hardware (e.g. computer servers for both a database and the web site) and software (e.g., web server and database software).

During typical operation, the patient continuously wears the ABPM 20 for a period of time, ranging from a 1-2 days to weeks. For longer-term monitoring (e.g. several months), the patient may wear the ABPM 20 for shorter periods of time during the day. To view information sent from the ABPM 20, the patient or medical professional accesses a user interface hosted on the web site 66 through the Internet 67 from the secondary computer system 69. The system 53 may also include a call center, typically staffed with medical professionals such as doctors, nurses, or nurse practioners, whom access a care-provider interface hosted on the same website 66.

In an alternate embodiment, the host computer system 57 includes a web services interface 70 that sends information using an XML-based web services link to a secondary, web-based computer application 71. This application 71, for example, could be a data-management system operating at a hospital.

FIGS. 5A and 5B show an adhesive patch sensor 205 according to the invention that features a pair of LEDs 210, 212 and photodetector 214 that, when attached to a patient, generate an optical waveform (231 in FIG. 6). A horseshoe-shaped metal electrode 217 surrounds these optical components and generates an electrical waveform (232 in FIG. 6). The electrical and optical waveforms, once generated, pass through a cable 218 to a processing module, which analyzes them as described in detail below to measure a patient's systolic and diastolic blood pressure, heart rate, and pulse oximetry. The patch sensor 205 features an adhesive component 219 that adheres to the patient's skin and secures the LEDs 210, 212, photodetector 214, and electrode 21 7 in place to minimize the effects of motion.

During operation, the cable 218 snaps into a plastic header 216 disposed on a top portion of the patch sensor 205. Both the cable 218 and header 216 include matched electrical leads that supply power and ground to the LEDs 210, 212, photodetector 214, and electrode 219. The cable 218 and header 216 additionally supply a high-frequency electrical signal to the electrode that helps generate the electrical waveform. When the patch sensor 205 is not measuring optical and electrical waveforms (e.g., when the patient is sleeping), the cable 218 unsnaps from the header 216, while the sensor 205 remains adhered to the patient's skin. In this way a single sensor can be used for several days. After use, the patient removes and then discards the sensor 205.

To measure blood pressure, heart rate, and pulse oximetry, the LEDs 210, 212 generate, respectively, red and infrared radiation that irradiates an underlying artery. Blood volume increases and then decreases as the heart pumps blood through the patient's artery. Blood cells within the blood absorb and transmit varying amounts of the red and infrared radiation depending the on the blood volume and how much oxygen binds to the cells' hemoglobin. The photodetector 214 detects a portion of the radiation that reflects off an underlying artery, and in response sends a radiation-induced photocurrent to an analog-to-digital converter embedded within the processing component. The analog-to-digital converter digitizes the photocurrent to generate a time-dependent optical waveform for each wavelength. In addition, the microprocessor analyzes waveforms generated at both red and infrared wavelengths, and compares a ratio of the relative absorption to a calibration table coded in its firmware to determine pulse oximetry. The microprocessor additionally analyzes the time-dependent properties of one of the optical waveforms to determine the patient's heart rate.

Concurrent with measurement of the optical waveform, the electrode 219 detects an electrical impulse from the patient's skin that the processing component processes to generate an electrical waveform. The electrical impulse is generated each time the patient's heart beats.

The patch sensor 205 preferably has a diameter, 'D', ranging from 0.5 centimeter ('cm') to 10 cm, more preferably from 1.5 cm to 3.0 cm, and most preferably 2.5 cm. The patch sensor 205 preferably has a thickness, 'T', ranging from 1.0 millimeter ("mm") to 3 mm, more preferably from 1.0 mm to 1.5 mm, and most preferably 1.25 mm. The patch sensor 205 preferably includes a body composed of a polymeric material such as a neoprene rubber. The body is preferably colored to match a patient's skin color, and is preferably opaque to reduce the affects of ambient light. The body is preferably circular in shape, but can also be non-circular, e.g. an oval, square, rectangular, triangular or other shape.

FIG. 6 shows both optical 231 and electrical 232 waveforms generated by the patch sensor of FIGS. 5A and 5B and used in the calibration procedure described above. Following a heartbeat, the electrical impulse travels essentially instantaneously from the patient's heart to the patch sensor, where the electrode detects it to generate the electrical waveform 232. At a later time, a pressure wave induced by the same heartbeat propagates through the patient's arteries and arrives at the sensor, where the LEDs and photodetector detect it as described above to generate the optical waveform 231. The propagation time of the electrical impulse is independent of blood pressure, whereas the propagation time of the pressure wave depends strongly on pressure, as well as mechanical properties of the patient's arteries (e.g., arterial size, stiffness). The microprocessor runs an algorithm that analyzes the time difference $\Delta T$ between the arrivals of these signals, i.e. the relative occurrence of the optical 231 and electrical 232 waveforms as measured by the patch sensor.

In still other embodiments, the above-described system can receive inputs from other measurement devices, such as weight scales, glucometers, EKG/ECG monitors, cuff-based blood pressure monitors, dietary monitors, pedometers and other exercise monitors, and GPS systems.

Still other embodiments are within the scope of the following claims.

What is claimed is:

1. A system for continuously monitoring an ambulatory patient's blood pressure, comprising:
    a patch sensor that attaches to the patient's skin, comprising: i) an optical sensor comprising at least one light source and a photodetector configured to detect radiation reflected from the patient's blood vessel and configured to generate an optical signal; and ii) an electrode that substantially surrounds the optical sensor and is configured to detect an electrical impulse from a patient to generate an electrical signal; and,
    a processing component configured to be worn on the patient's body, the processing component in electrical communication with the patch sensor and housed in an enclosure and separated from the patch sensor through a cable, and comprising a microprocessor configured to: i) process the optical and electrical signals to generate optical and electrical waveforms; ii) operate an algorithm that continuously determines blood pressure values by processing the optical and electrical waveforms based on a time difference between the arrivals of these waveforms to determine a transit time; iii) receive and store pre-determined calibration parameters and blood pressure threshold values; iv) continuously calculate blood pressure values from the transit time and pre-determined calibration parameters; and v) determine an alert condition from the continuously monitored blood pressure values and the blood pressure threshold value;
    a wireless transceiver component comprised by the processing component and configured to transmit and receive information from a remote device, the wireless transceiver configured to: i) receive patient-specific calibration parameters describing a mathematical relationship between transit time and blood pressure; ii) receive blood pressure threshold values; and, iii) transmit blood pressure information; and,
    an alert system designed to identify alert conditions, the alert system comprising algorithms to: i) generate an alert based on the patient's high or low blood pressures; and ii) generate a visual and audio display of the alert condition.

2. The system of claim 1, wherein the algorithm of the microcontroller processes: 1) the electrical waveform to determine a heart rate value; 2) the optical waveform to determine a pulse oximetry value; and 3) the optical and electrical waveforms to determine a blood pressure value.

3. The system of claim 1, further comprising a drug-delivery system for administering a pharmaceutical compound to the patient in response to a blood pressure value.

* * * * *